United States Patent
Meng

(10) Patent No.: US 8,722,648 B2
(45) Date of Patent: May 13, 2014

(54) LIQUID PHARMACEUTICAL FORM OF ALKYLPHOSPHOCHOLINE AND METHOD FOR PREPARING SAME

(76) Inventor: Paul Meng, Vienna (AT)

( * ) Notice: Subject to any disclaimer, the term of this patent is extended or adjusted under 35 U.S.C. 154(b) by 0 days.

(21) Appl. No.: 13/382,457

(22) PCT Filed: Jul. 9, 2009

(86) PCT No.: PCT/EP2009/004984
§ 371 (c)(1),
(2), (4) Date: Jan. 5, 2012

(87) PCT Pub. No.: WO2011/003430
PCT Pub. Date: Jan. 13, 2011

(65) Prior Publication Data
US 2012/0115814 A1    May 10, 2012

(51) Int. Cl.
*A61K 31/685* (2006.01)
*A01N 57/34* (2006.01)

(52) U.S. Cl.
USPC .............. 514/77; 514/75; 514/78; 424/57

(58) Field of Classification Search
USPC .......................................... 514/77
See application file for complete search history.

(56) References Cited

U.S. PATENT DOCUMENTS

2002/0173489 A1    11/2002 Eibl
2007/0264206 A1*  11/2007 Boga et al. ...................... 424/57
2009/0130029 A1    5/2009 Tamarkin et al.

FOREIGN PATENT DOCUMENTS

| CA | 2026278 A | * | 3/1991 |
| EP | 0534445 A1 | | 3/1993 |
| EP | 0916343 A1 | | 5/1999 |
| EP | 1214928 A1 | | 6/2002 |

* cited by examiner

*Primary Examiner* — Ernst Arnold
*Assistant Examiner* — Kyung Sook Chang
(74) *Attorney, Agent, or Firm* — Simana Rao, Esq.; McNeely, Hare & War LLP

(57) ABSTRACT

The inventions relates to a liquid pharmaceutical form containing an active ingredient alkylphosphocholines and a co-solvent system. The co-solvent system is mixture from hexylene glycol, propylene glycol, diethylene glycol monoethyl ether and water. The pharmaceutical form having a pH value in the range of 4 to 6, which if it is necessary can be achieved by adding a pH adjuster. The composition has a good storage stability and it is suitable for local application on the different organs of the body. The inventions relates also to a method for producing the same pharmaceutical form.

16 Claims, No Drawings

LIQUID PHARMACEUTICAL FORM OF ALKYLPHOSPHOCHOLINE AND METHOD FOR PREPARING SAME

CROSS-REFERENCE TO RELATED APPLICATIONS

This application claims priority to PCT International Application No. PCT/EP2009/004984 filed on Jul. 9, 2009, and published as WO 2011/003430, the application being incorporated herein in its entirety by reference.

FIELD OF THE INVENTION

The invention relates to a liquid pharmaceutical form comprising alkylphosphocholine intended for local application. The invention also relates to a method for preparing such composition.

PRIOR ART

Alkylphosphocholines are known substances. They are phosphocholine esters of aliphatic long chain alcohols differing in chain length, unsaturation and position of the cis-double bond. These compounds, as well as their excellent antitumor and antiprotozoal action, are described in European patent application EP0108565. Their most important and therapeutically relevant property is their antitumor efficacy, mainly directed against chemically induced mammary carcinomas, which has been proved experimentally (Hilgard et al. 1993; Zeisig et al. 1991, 1993) and in clinical trials (Unger and Eibl 1991; Dummer et al. 1993). The main representative of this class of substances is hexadecylphosphocholine. It has already been clinically applied in the treatment of cutaneous metastasis of breast cancer.

Topical treatment of skin metastases with liquid pharmaceutical form of cytotoxic agent is known. This application is attractive for its easy self-administration and absence of major systemic interference. It is known that alkylphosphocholines, especially hexadecylphosphocholine exert its cytotoxicity by acting on the cell membrane phospholipids and can be administrated topically. European patent EP0534445 describes the liquid medicament for topical administration suitable for the treatment of protozoal diseases, especially leishmaniasis, which contains as active ingredient any of the well-known alkylphosphocholines.

An object of protection under European patent EP0248047 is a medicament which is suitable for the topical application of tumors sensitive to treatment with an active compound hexadecylphosphocholine. The composition according to this invention comprises a mixture, also called a cascade, which contains hexadecylphosphocholine, and a solvent—aqueous mixture of three alkylglycerol ethers, namely, a low one, a medium one and a higher one whereby the amount by weight of the lower ether is about as great as the sum of amounts by weight of the two other ethers as well as possibly phenoxyethanol.

The medicament is prepared by dissolving hexadecylphosphocholine in the mixture of three alkylglycerol ethers, water, as well as possibly phenoxyethanol at the temperatures between 20-120° C. The obtained solution is freed.

The European patent EP0593897 describes a stabilized solution of alkylphosphocholines. The inventors Engle et al. indicate that the liquid pharmaceutical form of alkyl glycerol ethers with alkylphosphonic acids doesn't have storage stability. They discover that oxidative processes caused peroxides, which later led to acid and hence to a drop in pH due to further decomposition. Accordingly the inventions uses a buffer with pH 5.3 to enhance the stability of the solution. The preferred buffer is citrate buffer. The final solution of alkylphosphocholines has pH 4÷6.

The method of production of the stabilized solution of alkylphosphocholines consists of two steps. During the first step of the process the buffer aqueous solution with pH value of 5.3 is prepared. During the second step of the method the buffer solution obtained is mixed with the alkylphosphocholine dissolved in the three glycerol ethers-water mixture. The uniform solution is obtained with nitrogen gassing, filtered and dispensed into bottles.

A disadvantage of this composition is the solvents—alkyl glycerol ethers, which are not described in the pharmacopoeias and not available on the market and the necessity of additional stabilization of the solution that make the process of its production complicated to perform.

DISCLOSURE OF THE INVENTION

The present invention relates to a liquid pharmaceutical solution of alkylphosphocholines, suitable for local administration. The composition contains from 0.5 mg/ml to 300 mg/ml alkylphosphocholine, as an active ingredient, and a co-solvent system. The co-solvent system, which is used in the present invention, is a mixture from hexylene glycol, propylene glycol, diethylene glycol monoethyl ether and water. If it is necessary the solution obtained is acidified or alkalized to pH from about 4 to about 6.

The co-solvent system, which is used in the present invention, comprises from 2 to 50% v/v of hexylene glycol, from 40 to 46% v/v of propylene glycol, from 2 to 25% v/v of diethylene glycol monoethyl ether and form 10 to 50% v/v of water. According to a preferred embodiment of the invention the co-solvent system comprises 22% v/v of hexylene glycol, 44% v/v of propylene glycol, 2% v/v of diethylene glycol monoethyl ether and 32% v/v of water.

The alkylphosphocholines are soluble in water, ethanol and methanol, but there are accurate bibliography data missing. Our experiments showed that the solubility of alkylphosphocholines in particular solvents separately is not sufficient to obtain clear solution with the concentration and quality necessary for the locally applicable drug product. It has been also found that solubility of alkylphosphocholines will be considerably higher in a co-solvent system. For example, the solubility of alkylphosphocholines is sufficiency high in glycols and glycol ether. The improvement of alkylphosphocholines solubility is observed in propylene glycol-hexylene glycol-water mixtures as the solubility of alkylphosphocholines increases with increasing hexylene glycol concentration. The maximum is at 50% hexylene glycol level. The result indicated that the systems with 22% hexylene glycol level have greater effect in increasing alkylphosphocholines solubility. The alkylphosphocholines solubility response is linear in the propylene glycol-concentration range 40÷60% in the co-solvent mixture.

The addition of Transcutol P to the co-solvent mixture increased the solubility of alkylphosphocholines as a function of the concentration of Transcutol P, which may be due to a co-solvency effect. The functions of Transcutol P are simultaneously solubilizer and penetration enhancer to enable the active agent to cross the barrier of the stratum corneum.

Table 1 lists the enhanced solubilities of hexadecylphosphocholine in the disclosed co-solvent system and shows the cumulative effect of the addition of several adjunctive components of the system.

TABLE 1

Effect of the adjuctive components on the solubility of hexadecylphosphocholine at 25° C.

| Solvents (% v/v) | | | | Solubility (mg/ml) |
|---|---|---|---|---|
| Hexylene glycol 1 | Propylene glycol 2 | Transcutol P 3 | Water 4 | 5 |
| 22 | 0 | 0 | 78 | 118.7 |
| 22 | 44 | 0 | 34 | 138.3 |
| 22 | 44 | 2 | 32 | 152.9 |

A similar result is found for the other alkylphospholcholines tested in this experiment.

The co-solvent system, according to the invention, is selected from solvents which indicate better solubility of alkylphosphocholines, good antibacterial and fungistatic properties and good penetration enhancer. Therefore is not necessary to add preservatives to the solution, according to the invention, because the solvents in the co-solvent system have antiseptic properties.

According to a preferred embodiment of the invention, the concentration of the active ingredient in the liquid pharmaceutical composition is 60 mg/ml.

According to yet another favorable embodiment of the invention an active ingredient in the liquid pharmaceutical solution is hexadecylphosphocholine.

The pharmaceutical solution may contain trisodium citrate or citric acid anhydrous as pH adjuster depending on the pH value of batch alkylphosphocholine substance. For the production of aqueous solution of alkylphosphovholines no buffering agent is needed in order to maintain pH within limits.

It is further object of the present invention to provide a method for the production of the liquid pharmaceutical composition described so far. This method consists in dissolving alkylphospholine in the mixture of propylene glycol, hexylene glycol and diethylene glycol monoethyl ether by stirring. The pH value of the solution obtained is measured and is acidified or alkalized to pH 4÷6, if it is necessary. After the addition of the water, the solution obtained is mixed and then is left for defoaming. The liquid pharmaceutical product obtained is filtered through a membrane filter and the filtrate obtained is dispensed in portions.

An aqueous solution of trisodium citrate or aqueous citric acid anhydrous solution can be used to adjust pH value in the range 4-6.

Advantages of the liquid pharmaceutical form, according to the invention are the production of liquid pharmaceutical solution of alkylphosphocholine with high physical, chemical and microbial stability during storage, with good penetration effect, by using only pharmacopeia recipients available on the market and a simplified method of production.

EXAMPLES FOR PERFORMANCE OF THE INVENTION

The invention is described by the following examples:

Example 1

The composition of 100 ml of pharmaceutical solution of hexadecylphosphocholine (INN miltefosine) 60 mg/ml intended for local application is as follows:

| Ingredients | Quantity, mg/ml | Water, % | Quantity g |
|---|---|---|---|
| Miltefosine (F048TR0401) | 60.00 | 5.54 | 6.352 |
| Propylene glycol | 425.58 | | 42.558 |
| Hexylene glycol | 184.00 | | 18.400 |
| Diethylene glycol monoethyl ether | 19.74 | | 1.974 |
| Trisodium citrate | — | | — |
| Purified water up to ml | 1.0 | | 100.0 |

Miltefosine substance is sieved through a screen with a size of 0.5 mm and it is dissolved in a mixture of 42.558 g propylene glycol, 18.400 g hexylene glycol and 1.974 g Diethylene glycol monoethyl ether in a 100 ml graduated flask for 10 min. The pH of the miltefosine solution obtained is measured. pH value of the solution is 5.5 (range 4.0÷6.0). Water is added to make up to 100 ml solution. The solution obtained is mixed for 15 min and then is left for 30 min for defoaming. The pharmaceutical composition obtained is filtered through a membrane filter pore size 0.45 μm. The bulk solution is tested and dispensed in 10 ml portions into brown dropper bottles and closed with protective cap.

Example 2

The composition of 5 l of pharmaceutical solution of hexadecylphosphocholine (INN miltefosine) 60 mg/ml intended for local application is as follows:

| Composition | Quantity kg |
|---|---|
| Miltefosine* (F048TR0401) | 0.3176 |
| Propylene glycol | 2.1279 |
| Hexylene glycol | 0.9200 |
| Diethylene glycol monoethyl ether | 0.0987 |
| Trisodium citrate | 0.0005 |
| Purified water | 1.5760 |

*Note:
The quantity of miltefosine is calculated with the content of water 5.28%; the weight per millilitre of miltefosine solution is 1.008 g/ml.

The miltefosine substance is sieved through a screen with a size of 0.5 mm. In a vessel (stainless steel, Erweka planetary stirrer, PRS, V=5 l) 2.1279 kg propylene glycol, 0.92 kg hexylene glycol and 0.0987 kg Diethylene glycol monoethyl ether are mixed for 10 min. Miltefosine is dissolved in this mixture of glycols for 60 min. The pH of the miltefosine solution obtained is measured, after that a solution prepared from 0.0005 kg trisodium citrate in 1.5760 kg water (range 4.0÷6.0) is added slowly. The solution obtained is mixed for 30 min and then is left 30 min for defoaming. The pharmaceutical composition obtained is filtered through a membrane filter pore size 0.45 μm. The bulk solution is tested and dispensed in 10 ml portions into brown dropper bottles and closed with protective cap.

Example 3

The composition of 100 ml of pharmaceutical solution of hexadecylphosphocholine (INN miltefosine) 30 mg/ml intended for local application is as follows:

| Ingredients | Quantity, mg/ml | Water, % | Quantity g |
|---|---|---|---|
| Miltefosine (F048TR0401) | 30.00 | 5.54 | 3.176 |
| Propylene glycol | 425.58 | | 42.558 |
| Hexylene glycol | 184.00 | | 18.400 |
| Diethylene glycol monoethyl ether | 19.74 | | 1.974 |
| Purified water up to ml | 1.0 | | 100.0 |

The method of preparing the pharmaceutical solution of this example is the same as is given above in Example 1.

Example 4

The composition of 100 ml of pharmaceutical solution of hexadecylphosphocholine (INN miltefosine) 120 mg/ml intended for local application is as follows:

| Ingredients | Quantity, mg/ml | Water, % | Quantity g |
|---|---|---|---|
| Miltefosine (F048TR0401) | 120.00 | 5.54 | 12.704 |
| Propylene glycol | 425.58 | | 42.558 |
| Hexylene glycol | 184.00 | | 18.400 |
| Diethylene glycol monoethyl ether | 19.74 | | 1.974 |
| Purified water up to ml | 1.0 | | 100.0 |

The method of preparing the pharmaceutical solution of this example is the same as is given above in Example 1.

Example 5

The composition of 100 ml of pharmaceutical solution of hexadecylphosphocholine (INN miltefosine) 60 mg/ml is as follows:

| Ingredients | Quantity, mg/ml | Water, % | Quantity g |
|---|---|---|---|
| Miltefosine (F048TR0401) | 60.00 | 5.54 | 6.352 |
| Propylene glycol | 425.58 | | 42.558 |
| Hexylene glycol | 117.00 | | 11.700 |
| Diethylene glycol monoethyl ether | 19.74 | | 1.974 |
| Purified water up to ml | 1.0 | | 100.0 |

The method of preparing the pharmaceutical solution of this example is the same as is given above in Example 1.

Example 6

The pharmaceutical solution in the Example 1 is put on stability testing at 25° C./60% RH for 12 months of storage and at 40° C./75% RH for 6 months of storage. The analytical results are shown in the table 2.

TABLE 2

Results from stability testing of pharmaceutical solution of hexadecylphosphocholine

| Tests | Time of storage (months) | | | | |
|---|---|---|---|---|---|
| | 0 | 3 | 6 | 9 | 12 |
| Storage condition 25° C./60% RH | | | | | |
| Appearance | clear | comply | comply | comply | comply |
| Color of solution | colorless | colorless | colorless | colorless | colorless |
| Clarity of solution | clear | clear | clear | clear | clear |
| Identification(TLS) | comply with the test | comply | comply | comply | comply |
| pH | 4.29 | 4.28 | 4.25 | 4.27 | 4.23 |
| Assay, mg/ml | 60.45 | 60.34 | 60.38 | 60.39 | 60.36 |
| Related substances (TLC): | | | | | |
| Single impurity (%) | <0.2 | <0.2 | <0.2 | <0.2 | <0.2 |
| Total impurities (%) | <0.6 | <0.6 | <0.6 | <0.6 | <0.6 |
| Microbiological quality | In compliance with Ph.Eur. | comply | comply | comply | comply |
| Storage condition 40° C./75% RH | | | | | |
| Appearance | comply | comply | comply | | |
| Color of solution | colorless | colorless | colorless | | |
| Clarity of solution | clear | clear | clear | | |
| Identification(TLS) | comply | comply | comply | | |
| pH | 4.29 | 4.27 | 4.22 | | |
| Assay, mg/ml | 60.45 | 60.35 | 60.34 | | |
| Related substances (TLC): | | | | | |
| Single impurity (%) | <0.2 | <0.2 | <0.2 | | |
| Total impurities (%) | <0.6 | <0.6 | <0.6 | | |
| Microbiological quality | comply | comply | comply | | |

The invention claimed is:

1. A stable liquid pharmaceutical composition for local application comprising an alkylphosphocholine and a solvent, the composition having a concentration of the alkylphosphocholine of from 0.5 mg/ml to 300 mg/ml, the solvent comprises a co-solvent system consisting essentially of a mixture of hexylene glycol, propylene glycol, diethylene glycol monoethyl ether and water, and the solution has a pH in the range of from 4 to 6, wherein the composition excludes a buffer.

2. The liquid pharmaceutical composition according to claim 1, wherein the co-solvent mixture comprises from 2 to 50% v/v of hexylene glycol, from 40 to 46% v/v of propylene glycol, from 2 to 25% v/v of diethylene glycol monoethyl ether and from 10 to 50% v/v of water.

3. The liquid pharmaceutical composition according to claim 1, wherein the co-solvent mixture comprises 22%, v/v of hexylene glycol, 44% v/v of propylene glycol, 2% v/v of diethylene glycol monoethyl ether and 32% v/v of water.

4. The liquid pharmaceutical composition according to claim 1, wherein the concentration of alkylphosphocholine is 60 mg/ml.

5. The liquid pharmaceutical composition according to claim 1, wherein the alkylphosphocholine is hexadecylphosphocholine.

6. The liquid pharmaceutical composition according to claim 1, which further comprises a pH adjuster selected from trisodium citrate or citric acid anhydrous.

7. A process for preparing a liquid pharmaceutical composition for local application according to claim 1, wherein:
the alkyl phosphocholine is dissolved in a mixture of propylene glycol, hexylene glycol and diethylene glycol monoethyl ether by stirring,
the solution obtained is measured to obtain the pH value,
water is added to the solution, mixed and left for defoaming, and
the pharmaceutical composition obtained is filtered through a membrane filter and the filtrate obtained is dispensed in portions.

8. The process for preparing a liquid pharmaceutical composition according to claim 7, wherein after measurement of the pH value the solution is acidified or alkalized to obtain a pH of between 4 and 6, if necessary, with aqueous solution of trisodium citrate or aqueous citric acid anhydrous solution.

9. The liquid pharmaceutical composition of claim 1, wherein the composition is free of a preservative.

10. A method of treating a condition, the method comprising topically applying to a subject in need thereof a pharmaceutical composition of claim 1, the condition comprising one or more of a tumor, a protozoal disease, a carcinoma, breast cancer and skin metastases.

11. The method of claim 10, wherein the co-solvent mixture comprises from 2 to 50% v/v of hexylene glycol, from 40 to 46% v/v of propylene glycol, from 2 to 25% v/v of diethylene glycol monoethyl ether and from 10 to 50% v/v of water.

12. The method of claim 10, wherein the co-solvent mixture comprises 22%, v/v of hexylene glycol, 44% v/v of propylene glycol, 2% v/v of diethylene glycol monoethyl ether and 32% v/v of water.

13. The method of claim 10, wherein the concentration of alkylphosphocholine is 60 mg/ml.

14. The method of claim 10, wherein the alkylphosphocholine is hexadecylphosphocholine.

15. The liquid pharmaceutical composition according to claim 10, which further comprises a pH adjuster selected from trisodium citrate or citric acid anhydrous.

16. The method of claim 10, wherein the protozoal disease comprises leishmaniasis.

* * * * *